US012751618B2

(12) United States Patent
Yamada et al.

(10) Patent No.: US 12,751,618 B2
(45) Date of Patent: Oct. 6, 2026

(54) OPHTHALMIC OBSERVATION APPARATUS

(71) Applicant: Topcon Corporation, Tokyo (JP)

(72) Inventors: Kazuhiro Yamada, Tokyo (JP); Kazuhiro Oomori, Tokyo (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 353 days.

(21) Appl. No.: 18/033,802

(22) PCT Filed: Dec. 9, 2020

(86) PCT No.: PCT/JP2020/045755
§ 371 (c)(1),
(2) Date: Apr. 26, 2023

(87) PCT Pub. No.: WO2022/091429
PCT Pub. Date: May 5, 2022

(65) Prior Publication Data
US 2023/0397809 A1 Dec. 14, 2023

Related U.S. Application Data

(60) Provisional application No. 63/106,087, filed on Oct. 27, 2020.

(51) Int. Cl.
*A61B 3/13* (2006.01)
*A61B 3/117* (2006.01)
(Continued)

(52) U.S. Cl.
CPC ................ *A61B 3/13* (2013.01); *A61B 3/117* (2013.01); *A61B 3/12* (2013.01); *A61B 3/14* (2013.01);
(Continued)

(58) Field of Classification Search
CPC ............ A61B 3/0025; A61B 3/13–145; G02B 21/365; H04N 23/71; H04N 23/74;
(Continued)

(56) References Cited

U.S. PATENT DOCUMENTS 5,579,772 A 12/1996 Kinukawa et al.
10,251,783 B2 4/2019 Chernyak
(Continued)

FOREIGN PATENT DOCUMENTS

CN 101268928 A 9/2008
CN 103784117 A 5/2014
(Continued)

OTHER PUBLICATIONS

Japanese Office Action issued Aug. 20, 2024, in corresponding Japanese Application No. JP 2022-558821, 6pp.
(Continued)

*Primary Examiner* — Wyatt A Stoffa
*Assistant Examiner* — Samanvitha Sridhar
(74) *Attorney, Agent, or Firm* — XSENSUS LLP

(57) ABSTRACT

An ophthalmic observation apparatus of an embodiment includes a microscope, a processor, and a display controller. The microscope includes a pair of photography systems and is configured to acquire a pair of pieces of moving image data of a subject's eye. The processor is configured to perform first processing including at least one of a control of the microscope and image processing applied to at least one of the pair of pieces of moving image data, such that a predetermined parameter of the pair of pieces of moving image data satisfies a first condition. The display controller is configured to display a pair of moving images based on the pair of pieces of moving image data produced by the first processing on a display device.

9 Claims, 6 Drawing Sheets

(51) Int. Cl.

| | |
|---|---|
| ***A61B 3/12*** | (2006.01) |
| ***A61B 3/14*** | (2006.01) |
| ***A61B 3/15*** | (2006.01) |
| ***G02B 21/00*** | (2006.01) |
| ***G02B 21/36*** | (2006.01) |
| ***G06T 7/00*** | (2017.01) |
| ***H04N 23/67*** | (2023.01) |
| ***H04N 23/71*** | (2023.01) |
| ***H04N 23/74*** | (2023.01) |
| ***H04N 23/76*** | (2023.01) |
| *A61B 90/00* | (2016.01) |

(52) U.S. Cl.
CPC ................ *A61B 3/145* (2013.01); *A61B 3/15* (2013.01); *A61B 3/152* (2013.01); *G02B 21/0012* (2013.01); *G02B 21/365* (2013.01); *G06T 7/0012* (2013.01); *G06T 7/97* (2017.01); *H04N 23/67* (2023.01); *H04N 23/71* (2023.01); *H04N 23/74* (2023.01); *H04N 23/76* (2023.01); *A61B 2090/0807* (2016.02); *G06T 2207/10016* (2013.01); *G06T 2207/10056* (2013.01); *G06T 2207/30041* (2013.01); *G06T 2207/30168* (2013.01)

(58) Field of Classification Search
CPC . H04N 23/76; G06T 7/97; G06T 2207/10016; G06T 2207/30168
See application file for complete search history.

(56) References Cited

U.S. PATENT DOCUMENTS

| | | | | |
|---|---|---|---|---|
| 10,369,053 | B2 | 8/2019 | Srinivasan et al. | |
| 2002/0026179 | A1 | 2/2002 | Toh | |
| 2004/0004694 | A1 | 1/2004 | Sugino et al. | |
| 2005/0073647 | A1 | 4/2005 | Mihashi et al. | |
| 2006/0247659 | A1 | 11/2006 | Moeller et al. | |
| 2007/0047072 | A1 | 3/2007 | Zimmer | |
| 2008/0123053 | A1 | 5/2008 | Mihashi et al. | |
| 2008/0198219 | A1 | 8/2008 | Yoshida et al. | |
| 2009/0122398 | A1 | 5/2009 | Machida et al. | |
| 2009/0190092 | A1 | 7/2009 | Tsukada et al. | |
| 2009/0244483 | A1 | 10/2009 | Yoshino et al. | |
| 2011/0122365 | A1 | 5/2011 | Kraus et al. | |
| 2011/0153013 | A1 | 6/2011 | Moeller et al. | |
| 2011/0157553 | A1 | 6/2011 | Moeller et al. | |
| 2011/0230751 | A1 | 9/2011 | Kersting | |
| 2011/0292340 | A1 | 12/2011 | Shimizu et al. | |
| 2011/0304819 | A1 | 12/2011 | Juhasz et al. | |
| 2012/0050672 | A1 | 3/2012 | Aikawa | |
| 2012/0197102 | A1 | 8/2012 | Hanebuchi et al. | |
| 2013/0110092 | A1 | 5/2013 | Yee | |
| 2013/0110093 | A1 | 5/2013 | Yee | |
| 2013/0110206 | A1 | 5/2013 | Yee et al. | |
| 2013/0116672 | A1 | 5/2013 | Yee | |
| 2013/0135582 | A1 | 5/2013 | Hanebuchi et al. | |
| 2014/0118687 | A1 | 5/2014 | Ohban et al. | |
| 2014/0146287 | A1 | 5/2014 | Ota | |
| 2014/0160429 | A1 | 6/2014 | Nakano et al. | |
| 2014/0228824 | A1 | 8/2014 | Yee et al. | |
| 2014/0300863 | A1 | 10/2014 | Fukuma et al. | |
| 2015/0046094 | A1 | 2/2015 | Chaudhary et al. | |
| 2015/0077528 | A1 | 3/2015 | Awdeh | |
| 2015/0272435 | A1 | 10/2015 | Ito et al. | |
| 2015/0342460 | A1* | 12/2015 | Izatt | A61B 5/0073 600/425 |
| 2016/0095752 | A1 | 4/2016 | Srinivasan et al. | |
| 2016/0128871 | A1 | 5/2016 | Yee | |
| 2016/0157710 | A1 | 6/2016 | Tomatsu et al. | |
| 2016/0228295 | A1 | 8/2016 | Yee et al. | |
| 2016/0291257 | A1 | 10/2016 | Huang et al. | |
| 2017/0151089 | A1 | 6/2017 | Chernyak | |
| 2017/0280989 | A1* | 10/2017 | Heeren | A61B 3/10 |
| 2017/0281405 | A1 | 10/2017 | Ha | |
| 2017/0303782 | A1 | 10/2017 | Ito et al. | |
| 2017/0304119 | A1 | 10/2017 | Yee | |
| 2018/0049840 | A1* | 2/2018 | Awdeh | A61B 90/20 |
| 2018/0098812 | A1 | 4/2018 | Ootsuki | |
| 2018/0125361 | A1 | 5/2018 | Okuda | |
| 2018/0228431 | A1 | 8/2018 | Chaudhary et al. | |
| 2019/0076012 | A1 | 3/2019 | Kobayashi | |
| 2019/0091008 | A1 | 3/2019 | Ishikawa | |
| 2019/0104921 | A1 | 4/2019 | Yamamoto | |
| 2019/0192251 | A1 | 6/2019 | Kado et al. | |
| 2019/0357980 | A1 | 11/2019 | Andrews et al. | |
| 2020/0146885 | A1 | 5/2020 | Ootsuki et al. | |
| 2020/0214562 | A1 | 7/2020 | Kawasaki et al. | |
| 2020/0237213 | A1 | 7/2020 | Ono et al. | |
| 2020/0306002 | A1 | 10/2020 | Kamata | |
| 2020/0311918 | A1 | 10/2020 | Loerner | |
| 2021/0401369 | A1 | 12/2021 | Chaudhary et al. | |
| 2022/0115122 | A1 | 4/2022 | Enoki et al. | |
| 2022/0148165 | A1 | 5/2022 | Ootsuki et al. | |
| 2022/0386869 | A1 | 12/2022 | Ono et al. | |

FOREIGN PATENT DOCUMENTS

| | | | | | |
|---|---|---|---|---|---|
| CN | 104939802 | A | | 9/2015 | |
| DE | 202013011877 | U1 | | 9/2014 | |
| EP | 3491996 | A1 | | 6/2019 | |
| JP | 2001-276111 | A | | 10/2001 | |
| JP | 3354627 | B2 | | 12/2002 | |
| JP | 2003-310556 | A | | 11/2003 | |
| JP | 2006136714 | A | | 6/2006 | |
| JP | 2006280612 | A | | 10/2006 | |
| JP | 2007-028295 | A | | 2/2007 | |
| JP | 2009-118955 | A | | 6/2009 | |
| JP | 2011191517 | A | * | 9/2011 | |
| JP | 2011528592 | A | | 11/2011 | |
| JP | 2012506272 | A | | 3/2012 | |
| JP | 2012152469 | A | | 8/2012 | |
| JP | 2013-027672 | A | | 2/2013 | |
| JP | 2014-068766 | A | | 4/2014 | |
| JP | 2014-534011 | A | | 12/2014 | |
| JP | 2016-182262 | A | | 10/2016 | |
| JP | 2016531666 | A | | 10/2016 | |
| JP | 2016209291 | A | | 12/2016 | |
| JP | 2016214781 | A | | 12/2016 | |
| JP | 2017-012430 | A | | 1/2017 | |
| JP | 2017029333 | A | * | 2/2017 | |
| JP | 2018-051210 | A | | 4/2018 | |
| JP | 2018051223 | A | | 4/2018 | |
| JP | 2019-013803 | A | | 1/2019 | |
| JP | 2019-092844 | A | | 6/2019 | |
| JP | 2019-162336 | A | | 9/2019 | |
| JP | 2020-116140 | A | | 8/2020 | |
| JP | 2020130607 | A | * | 8/2020 | H04N 23/698 |
| WO | 03/022138 | A1 | | 3/2003 | |
| WO | 2016/061454 | A1 | | 4/2016 | |
| WO | 2017/154348 | A1 | | 9/2017 | |
| WO | 2017175853 | A1 | | 10/2017 | |
| WO | 2017/221507 | A1 | | 12/2017 | |
| WO | 2018/207466 | A1 | | 11/2018 | |
| WO | 2019/059314 | A1 | | 3/2019 | |
| WO | 2020/179588 | A1 | | 9/2020 | |

OTHER PUBLICATIONS

Japanese Office Action issued Sep. 3, 2024, in corresponding Japanese Application No. JP 2022-558822, 6pp.

Japanese Office Action issued Oct. 22, 2024, in corresponding Japanese Application No. JP 2022-558823, 6pp.

Japanese Office Action issued Aug. 27, 2024, in corresponding Japanese Application No. JP 2022-558830, 6pp.

Extended European Search Report issued Sep. 18, 2024, in corresponding European Application No. 21885560.9, 8pp.

International Search Report and Written Opinion mailed on Mar. 2, 2021, received for PCT Application PCT/JP2020/045755, filed on Dec. 9, 2020, 8 pages including English Translation.

(56) References Cited

OTHER PUBLICATIONS

International Search Report and Written Opinion mailed on Jan. 19, 2021, received for PCT Application PCT/JP2020/045761, filed on Dec. 9, 2020, 10 pages including English Translation.
International Search Report and Written Opinion mailed on Feb. 2, 2021, received for PCT Application PCT/JP2020/045760, filed on Dec. 9, 2020, 9 pages including English Translation.
International Search Report and Written Opinion mailed on Mar. 9, 2021, received for PCT Application PCT/JP2020/045754, filed on Dec. 9, 2020, 9 pages including English Translation.
International Search Report and Written Opinion mailed on Mar. 23, 2021, received for PCT Application PCT/JP2021/003639, filed on Feb. 2, 2021, 8 pages including English Translation.
Japanese Office Action issued Jun. 18, 2025, in corresponding Japanese Patent Application No. 2022-558823, 6pp.
Chinese Office Action issued Dec. 20, 2024, in corresponding Chinese Patent Application No. 202080106764.2, 15pp.
Chinese Office Action issued Dec. 24, 2024, in corresponding Chinese Patent Application No. 202080106762.3, 18pp.
Chinese Office Action issued Dec. 31, 2024, in corresponding Chinese Patent Application No. 202080106760.4, 12pp.
Japanese Office Action issued Jan. 28, 2025, in corresponding Japanese Patent Application No. 2022-558820, 11pp.
Extended European Search Report issued Nov. 5, 2024, in corresponding European Patent Application No. 20959942.2, 8pp.
Extended European Search Report issued Nov. 7, 2024, in corresponding European Patent Application No. 20959943.0, 8pp.
Extended European Search Report issued Nov. 5, 2024, in corresponding European Patent Application No. 20959945.5, 9pp.
Communication pursuant to Article 94(3) EPC issued Jul. 10, 2025 in corresponding European Patent Application No. 20 959 943.0, 7pp.
Chinese Office Action issued Jul. 30, 2025, in corresponding Chinese Patent Application No. 202080106764.2, with Machine Translation by Global Dossier, 10pp.
Japanese Office Action issued Aug. 5, 2025, in corresponding Japanese Patent Application No. 2024-212100, with Machine Translation by Global Dossier, 10pp.
Office Action issued on Apr. 28, 2025, in corresponding European patent Application No. 21885560.9, 9 pages.
Office Action issued on Jun. 10, 2025, in corresponding European patent Application No. 20959945.5, 7 pages.
Office Action issued on Jun. 27, 2025, in corresponding European patent Application No. 20959942.2, 8 pages.
Office Action issued on Jun. 12, 2025, in corresponding Chinese patent Application No. 202080106760.4, 10 pages.
US Office Action issued Aug. 14, 2025 in related U.S. Appl. No. 18/033,812, 68pp.
US Office Action issued Jul. 2, 2025 in related U.S. Appl. No. 18/033,815, 66pp.
US Office Action issued Jul. 2, 2025 in related U.S. Appl. No. 18/033,821, 25pp.
US Office Action issued Jun. 12, 2025 in related U.S. Appl. No. 18/033,849, 8pp .
Communication pursuant to Article 94(3) EPC issued Nov. 7, 2025, in corresponding European Patent Application No. 20 959 945.5, 5pp.
Office Action issued Dec. 5, 2025, in corresponding U.S. Appl. No. 18/033,849, 9pp.
Communication pursuant to Article 94(3) EPC issued Dec. 8, 2025, in corresponding European Patent Application No. 20 959 942.2, 10pp.
Communication pursuant to Article 94(3) EPC issued Dec. 12, 2025, in corresponding European Patent Application No. 20 959 943.0, 4pp.
Office Action issued Dec. 16, 2025, in corresponding U.S. Appl. No. 18/033,815, 17pp.
Office Action issued Jan. 20, 2026, in corresponding Japanese Patent Application No. 2024-212100, 12pp.
Office Action issued Nov. 14, 2025, in corresponding U.S. Appl. No. 18/033,821, 17pp.
Communication pursuant to Article 94(3) EPC issued Oct. 1, 2025, in corresponding European Patent Application No. 21 885 560.9, 7pp.
Office Action (Rejection Decision) issued Feb. 6, 2026 in Chinese Patent Application No. 202080106760.4, 8 pages.
Office Action issued Feb. 11, 2026 in Chinese Patent Application No. 202180073485.5, 16 pages.
Office Action issued Apr. 2, 2026 in U.S. Appl. No. 18/033,815, 20 pages.
JP Decision of Refusal issued for the corresponding Japanese Patent Application No. 2024-212100, 2pp.
JP Decision of Dismissal of Amendment issued for the corresponding Japanese Patent Application No. 2024-212100, 7pp.
US Office Action issued Jul. 27, 2026 in related U.S. Appl. No. 18/033,849, 24pp.

* cited by examiner

OPHTHALMIC OBSERVATION APPARATUS

CROSS-REFERENCE TO RELATED APPLICATIONS

This application is a national stage (under 35 U.S.C. 371) of International Patent Application No. PCT/JP2020/045755, filed Dec. 9, 2020, claiming priority to U.S. Provisional Patent Application Ser. No. 63/106,087, filed Oct. 27, 2020, entitled "APPARATUS AND METHOD FOR OPHTHALMIC OBSERVATION", both of which are herein incorporated by reference in their entirety.

FIELD

The present disclosure relates generally to an ophthalmic observation apparatus.

BACKGROUND

An ophthalmic observation apparatus is an apparatus for observing an eye of a patient (which will be referred to as a subject's eye hereinafter). Ophthalmic observation is conducted to grasp the condition of the subject's eye in various situations such as examination, surgery, and treatment.

Conventional ophthalmic observation apparatuses are configured to provide a user with a magnified image formed by an objective lens, a variable magnification optical system, etc. via an eyepiece. In recent years, some ophthalmic observation apparatuses are configured to photograph a magnified image formed by an objective lens, a variable magnification optical system, etc. with an image sensor, and display the photographed image obtained (such an ophthalmic observation apparatus will be referred to as a digital ophthalmic observation apparatus). Examples of such digital ophthalmic observation apparatuses include surgical microscopes, slit lamp microscopes, and fundus cameras (retinal cameras). In addition, various kinds of ophthalmic examination apparatuses such as refractometers, keratometers, tonometers, specular microscopes, wavefront analyzers, and microperimeters are also provided with the function of the digital ophthalmic observation apparatus.

Generally, an ophthalmic observation apparatus is configured to provide an image of a subject's eye to a user (e.g., a health professional (health care practitioner, healthcare worker) such as a doctor). A typical digital ophthalmic observation apparatus is configured to perform photographing of a moving image using infrared light and/or visible light as illumination light, and real-time display of the moving image obtained by the moving image photography. The real-time moving image (video, movie, moving picture, etc.) provided in these ways is referred to as an observation image or a live image.

PATENT DOCUMENT 1: Japanese Unexamined Patent Application Publication No. 2019-162336

Methods (or techniques) of using a conventional eyepiece type (non-digital) binocular ophthalmic observation apparatus include a method of observing with different conditions for a pair of left and right optical systems. For example, in ophthalmic surgery using an eyepiece-type surgical microscope, the aperture of the first optical system is made smaller than the aperture of the second optical system, so that an image with a relatively deep (wide, large) depth of field (depth of focus) is observed through the first optical system while an image with a relatively high resolution (resolving power, definition) is observed through the second optical system. This enables the surgeon (operator) to conduct observation with a wide (deep) depth of field while ensuring the resolution quality of the observation image.

It is conceivable that such an observation method, which has been performed using a non-digital ophthalmic observation apparatus, could be applied to a digital ophthalmic observation apparatus. However, if the conditions of the left and right optical systems of a binocular digital ophthalmic observation apparatus are set to be different from each other, left and right photographed images obtained respectively by the left and right optical systems will differ greatly in appearance (representation, visual aspect). Therefore, displaying these images makes it difficult to perform observation properly. For example, if the diaphragm (aperture) conditions of the left and right optical systems are set to be different from one another, the brightness of the left photographed image and the brightness of the right photographed image will be significantly different from one another. Therefore, a situation arises in which the surgeon observes a bright image with one eye while observing a dark image with the other eye.

BRIEF SUMMARY

One object of the present disclosure is to provide a novel method or technique for using a digital ophthalmic observation apparatus.

An ophthalmic observation apparatus of some aspect examples includes: a microscope including a pair of photography systems and configured to acquire a pair of pieces of moving image data of a subject's eye; a processor configured to perform first processing including at least one of a control of the microscope and image processing applied to at least one of the pair of pieces of moving image data, such that a predetermined parameter of the pair of pieces of moving image data satisfies a first condition; and a display controller configured to display a pair of moving images based on the pair of pieces of moving image data produced by the first processing on a display device.

In the ophthalmic observation apparatus of some aspect examples, the processor may be configured to perform the first processing in such a manner as to compensate for a difference in the parameter of the pair of moving images caused by a difference in a predetermined photography condition between the pair of photography systems.

In the ophthalmic observation apparatus of some aspect examples, each of the pair of photography systems may include an image sensor, and a diaphragm configured for adjusting an amount of light directed to the image sensor, and the photography condition may include a condition of the diaphragm.

In the ophthalmic observation apparatus of some aspect examples, the processor may be configured to perform the first processing in such a manner as to compensate for a difference in brightness between the pair of moving images.

In the ophthalmic observation apparatus of some aspect examples, the processor may be configured to control a gain of the image sensor of at least one of the pair of photography systems in order to compensate for the difference in the brightness.

In the ophthalmic observation apparatus of some aspect examples, the processor may be configured to adjust brightness of at least one of the pair of pieces of moving image data in order to compensate for the difference in the brightness.

In the ophthalmic observation apparatus of some aspect examples, the processor may be configured to perform second processing including at least one of a control of the microscope and image processing applied to at least one of the pair of pieces of moving image data such that the brightness of the pair of moving images further satisfies a second condition.

In the ophthalmic observation apparatus of some aspect examples, the processor may be configured to perform the second processing such that the brightness of both the pair of moving images becomes equal to or greater than a predetermined threshold value.

In the ophthalmic observation apparatus of some aspect examples, the processor may be configured to perform the first processing in such a manner as to compensate for a difference in brightness between the pair of moving images.

These aspect examples allow a novel method or technique for using a digital ophthalmic observation apparatus to be provided.

DETAILED DESCRIPTION

Figure 1:
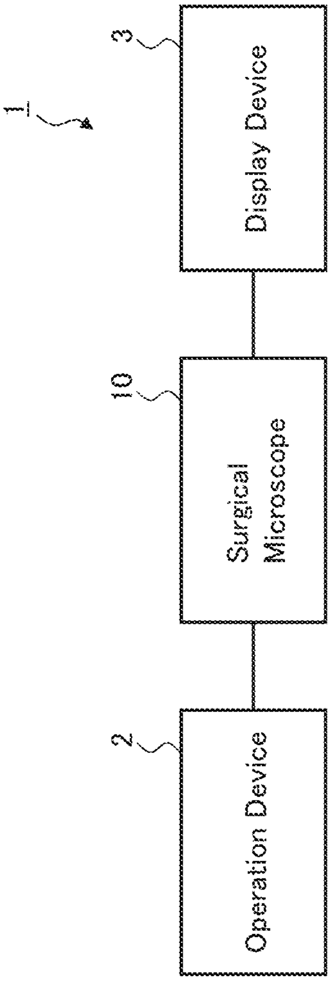
FIG. 1 is a diagram illustrating an example of a configuration of an ophthalmic observation apparatus (ophthalmic surgical microscope) according to an embodiment example.

Some aspect examples of an ophthalmic observation apparatus according to some embodiments will be described in detail with reference to the drawings. It should be noted that any of the matters and items described in the documents cited in the present disclosure and any known techniques and technologies may be combined with any of the aspect examples.

The ophthalmic observation apparatus according to some aspect examples is used in medical practice (healthcare practice) such as surgery, examination, and treatment of the subject's eye, in order to grasp (understand, recognize, find) the state of the subject's eye. The ophthalmic observation apparatus of the aspect examples described herein is mainly a surgical microscope system. However, ophthalmic observation apparatuses of embodiments are not limited to surgical microscope systems. For example, the ophthalmic observation apparatus of some aspect examples may be any of a slit lamp microscope, a fundus camera, a refractometer, a keratometer, a tonometer, a specular microscope, a wavefront analyzer, and a microperimeter. Also, the ophthalmic observation apparatus of some aspect examples may be a system that includes any one or more of these apparatus examples. More generally, the ophthalmic observation apparatus of some aspect examples may be any type of ophthalmic apparatus having an observation function.

A target ocular site for observation (ocular site to be observed, ocular site subject to observation) by using the ophthalmic observation apparatus may be any site of the subject's eye, and may be any site of the anterior segment and/or any site of the posterior segment. Examples of the observation target sites of the anterior segment include cornea, iris, anterior chamber, corner angle, crystalline lens, ciliary body, and zonule of Zinn. Examples of the observation target sites of the posterior segment include retina, choroid, sclera, and vitreous body. The observation target site is not limited to tissues of an eye ball, and may be any site subject to be observed in ophthalmic medical practice (and/or medical practice in other medical fields) such as eyelid, meibomian gland, and orbit (eye socket, eye pit).

At least one or more of the functions of the elements described in the present disclosure are implemented by using a circuit configuration (or circuitry) or a processing circuit configuration (or processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), a conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case where the hardware is a processor, which may be considered as a certain type of circuitry, then circuitry, a unit, a means, or a term similar to these is a combination of hardware and software. In this case, the software is used to configure the hardware and/or the processor.

<Ophthalmic Observation Apparatus>

FIG. 1 shows the configuration of the ophthalmic observation apparatus of some aspect examples.

The ophthalmic observation apparatus 1 (surgical microscope system, operation microscope system) according to the present embodiment includes the operation device 2, the display device 3, and the surgical microscope (operation microscope) 10. In some aspects, the surgical microscope 10 may include at least one of the operation device 2 and the display device 3. In some aspects, the display device 3 may not be included in the ophthalmic observation apparatus 1. In other words, the display device 3 may be a peripheral device of the ophthalmic observation apparatus 1.

<Operation Device 2>

The operation device 2 includes an operation device and/or an input device. For example, the operation device 2 may include any of a button, a switch, a mouse, a keyboard, a trackball, an operation panel, a dial, and the like. Typically, the operation device 2 includes a foot switch, like standard (general, normal, usual) ophthalmic surgical microscopes. Further, the operation device 2 may also be configured in such a manner that the user performs operations using voice recognition, line-of-sight (gaze) input, or like input technologies.

<Display Device 3>

The display device 3 displays an image of the subject's eye acquired by the surgical microscope 10. The display device 3 includes a display device such as a flat panel display. The display device 3 may include any of various kinds of display devices such as a touch panel. The display device 3 of some typical aspects includes a display device with a large screen. The display device 3 includes one or more display devices. In the case where the display device 3 includes two or more display devices, for example, one may be a display device with a relatively large screen and one of the other(s) may be a display device with a relatively small screen. Also, a configuration may be employed in which a plurality of display regions is provided in one display device to display a plurality of pieces of information.

The operation device 2 and the display device 3 do not have to be separate devices. For example, a device having both the operation function and the display function, such as a touch panel, may be used as the display device 3. In such a case, the operation device 2 may include a computer program in addition to the touch panel. A content of an operation made by the operation device 2 is sent to a processor (not shown in the drawings) as an electric signal. Further, a graphical user interface (GUI) displayed on the display device 3 and the operation device 2 may be used to conduct operations (instructions) and input information. In some aspects, the functions of the operation device 2 and the display device 3 may be implemented with a touch screen.

<Surgical Microscope 10>

The surgical microscope 10 is used for observation of the eye of a patient (subject's eye) in the supine position. The surgical microscope 10 performs photographing of the subject's eye to generate digital image data (moving image data). In particular, the surgical microscope 10 generates a moving image (video, movie) of the subject's eye. The moving image generated by the surgical microscope 10 is transmitted to the display device 3 through a wired and/or wireless signal path and displayed on the display device 3. The user (e.g., surgeon) can carry out surgery while observing the subject's eye through the displayed image (observation image, live image). In addition to such an observation mode through the moving image, the surgical microscope 10 of some aspects may be capable of providing observation through an eyepiece as in the past.

In some aspects, the surgical microscope 10 includes a communication device for transmitting and receiving electrical signals to and from the operation device 2. The operation device 2 receives an operation (instruction) performed by the user and generates an electric signal (operation signal) corresponding to the operation. The operation signal is transmitted to the surgical microscope 10 through a wired and/or wireless signal path. The surgical microscope 10 executes processing corresponding to the operation signal received.

<Optical System of Surgical Microscope 10>

An example of the configuration of the optical system of the surgical microscope 10 will be described. Below, directions are defined as follows, for convenience of description: the z direction is defined to be the optical axis direction (direction along the optical axis) of the objective lens (the z direction is, for example, the vertical direction, the up and down direction during surgery); the x direction is defined to be a predetermined direction perpendicular to the z direction (the x direction is, for example, the horizontal direction during surgery, and the left and right direction for the surgeon and the patient during surgery); and the y direction is defined to be the direction perpendicular to both the z and x directions (the y direction is, for example, the horizontal direction during surgery, the front and back direction for the surgeon during surgery, and the body axis direction (direction along the body axis) for the patient during surgery).

The observation optical system of the surgical microscope 10 includes a pair of optical systems. One of the optical systems acquires moving image data presented to the user's left eye, and the other of the optical systems acquires moving image data presented to the right eye. This allows the user to conduct observation with both eyes (binocular observation), particularly stereoscopic viewing (stereoscopic observation).

Figure 2:
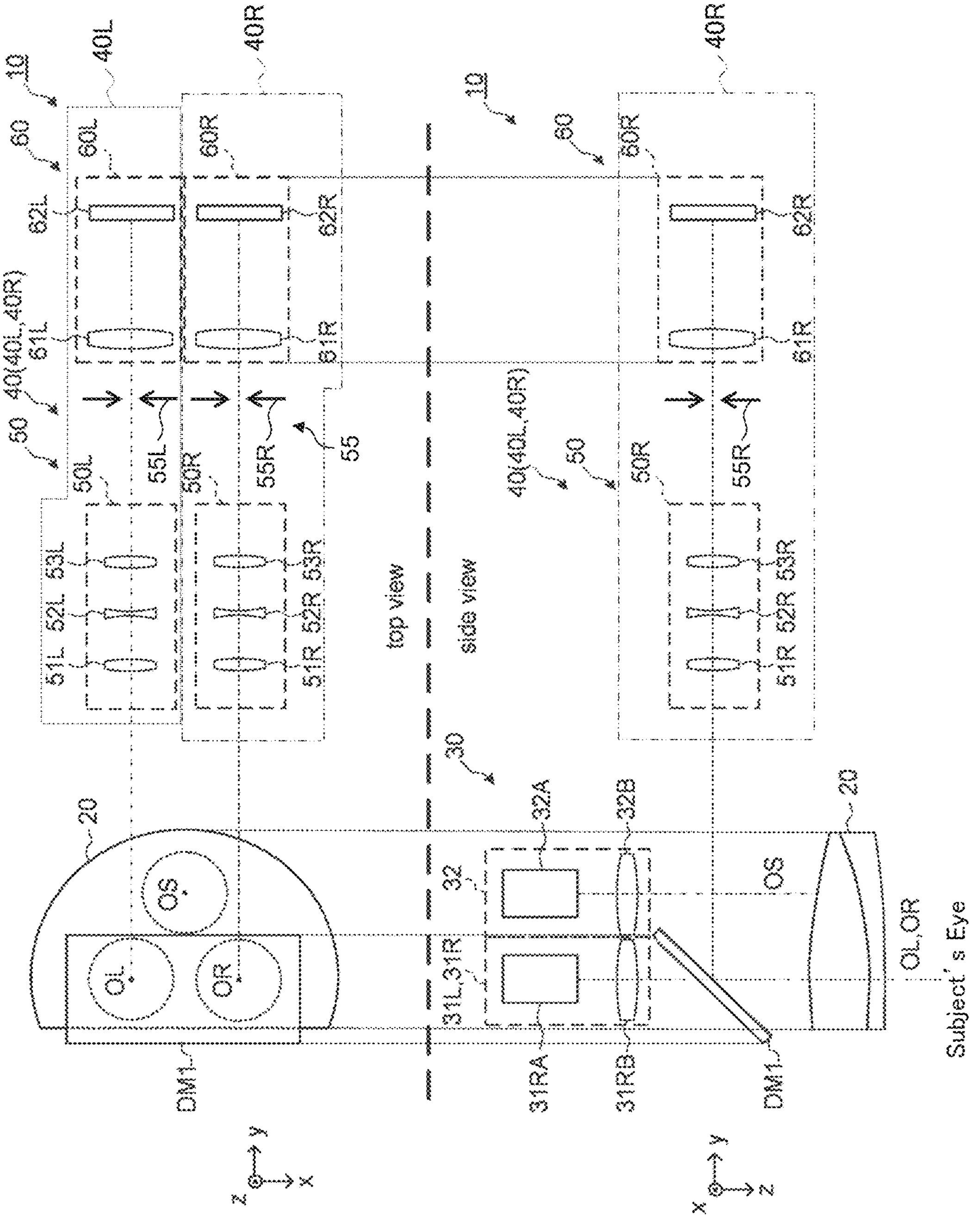
FIG. 2 is a diagram illustrating an example of a configuration of an ophthalmic observation apparatus according to an embodiment example.

FIG. 2 shows an example of the configuration of the optical system of the surgical microscope 10. FIG. 2 illustrates a schematic top view of the optical system viewed from above (top view) and a schematic side view of the optical system viewed from the side (side view) in association with each other. In order to simplify the illustration, the illumination optical system 30 arranged above the objective lens 20 is omitted in the top view.

The surgical microscope 10 includes the objective lens 20, the dichroic mirror DM1, the illumination optical system 30, and the observation optical system 40. The observation optical system 40 includes the zoom expander 50, the diaphragm 55, and the imaging camera 60. In some aspects, the illumination optical system 30 or the observation optical system 40 includes the dichroic mirror DM1.

The objective lens 20 is arranged to face the subject's eye. The objective lens 20 is arranged such that its optical axis is oriented along the z direction. The objective lens 20 may include two or more lenses.

The dichroic mirror DM1 couples the optical path of the illumination optical system 30 and the optical path of the observation optical system 40 with each other. The dichroic mirror DM1 is arranged between the illumination optical system 30 and the objective lens 20. The dichroic mirror DM1 transmits illumination light from the illumination optical system 30 and directs the illumination light to the subject's eye through the objective lens 20. Also, the dichroic mirror DM1 reflects return light from the subject's eye incident through the objective lens 20 and directs the return light to the imaging camera 60 of the observation optical system 40.

The dichroic mirror DM1 coaxially couples the optical path of the illumination optical system 30 and the optical path of the observation optical system 40 with each other. In other words, the optical axis of the illumination optical system 30 and the optical axis of the observation optical system 40 intersect at the dichroic mirror DM1. The illumination optical system 30 includes an illumination optical system for left eye (31L) and an illumination optical system for right eye (31R), and the observation optical system 40 includes an observation optical system for left eye (40L) and an observation optical system for right eye (40R). The dichroic mirror DM1 coaxially couples the optical path of the illumination optical system for left eye (the first illumination optical system 31L) and the optical path of the observation optical system for left eye (40L) with each other, and coaxially couples the optical path of the illumination optical system for right eye (the first illumination optical system 31R) and the optical path of the observation optical system for right eye (40R) with each other.

The illumination optical system 30 is an optical system for illuminating the subject's eye through the objective lens 20. The illumination optical system 30 may be configured to selectively illuminate the subject's eye with two or more pieces of illumination light having different color temperatures. The illumination optical system 30 projects illumination light having a designated color temperature onto the subject's eye under the control of a controller (the controller 200 described later).

The illumination optical system 30 includes the first illumination optical systems 31L and 31R and the second illumination optical system 32.

Each of the optical axis OL of the first illumination optical system 31L and the optical axis OR of the first illumination optical system 31R is arranged with the optical axis of the objective lens 20 in a substantially coaxial manner. Such arrangements enable a coaxial illumination mode and therefore make it possible to obtain a red reflex image (transillumination image) formed by utilizing diffuse reflection from eye fundus. The present aspect allows the red reflex image of the subject's eye to be observed with both eyes.

The second illumination optical system 32 is arranged in such a manner that its optical axis OS is eccentric (deviated, shifted) from the optical axis of the objective lens 20. The first illumination optical systems 31L and 31R and the second illumination optical system 32 are arranged such that the deviation of the optical axis OS with respect to the optical axis of the objective lens 20 is larger than the deviations of the optical axes OL and OR with respect to the optical axis of the objective lens 20. Such arrangements enable an illumination mode referred to as "angled illumination (oblique illumination)" and therefore enables binocular observation of the subject's eye while preventing ghosting caused by corneal reflection or the like. In addition, the arrangements enable detailed observation of unevenness and irregularities of sites and tissues of the subject's eye.

The first illumination optical system 31L includes the light source 31LA and the condenser lens 31LB. The light source 31LA outputs illumination light having a wavelength in the visible range (visible region) corresponding to color temperature of 3000 K (kelvins), for example. The illumination light emitted from the light source 31LA passes through the condenser lens 31LB, passes through the dichroic mirror DM1, passes through the objective lens 20, and then is incident on the subject's eye.

The first illumination optical system 31R includes the light source 31RA and the condenser lens 31RB. The light source 31RA also outputs illumination light having a wavelength in the visible range corresponding to color temperature of 3000 K, for example. The illumination light emitted from the light source 31RA passes through the condenser lens 31RB, passes through the dichroic mirror DM1, passes through the objective lens 20, and then is incident on the subject's eye.

The second illumination optical system 32 includes the light source 32A and the condenser lens 32B. The light source 32A outputs illumination light having a wavelength in the visible range corresponding to a color temperature within the range of 4000 K to 6000 K, for example. The illumination light emitted from the light source 32A passes through the condenser lens 32B, passes through the objective lens 20 without passing through the dichroic mirror DM1, and then is incident on the subject's eye.

In the present aspect example, the color temperature of the illumination light from the first illumination optical systems 31L and 31R is lower than the color temperature of the illumination light from the second illumination optical system 32. Such a configuration makes it possible to observe the subject's eye in warm colors using the first illumination optical systems 31L and 31R, and therefore enables detailed observation of the structure and morphology of the subject's eye.

In some aspects, each of the optical axes OL and OR is movable relative to the optical axis of the objective lens 20. The direction of the relative movement is a direction that intersects the optical axis of the objective lens 20, and the relative movement is represented by a displacement vector in which at least one of the x component and the y component is not zero. In some aspects, the optical axes OL and OR may be mutually independently movable. On the other hand, in some aspects, the optical axes OL and OR may be integrally movable. For example, the surgical microscope 10 includes a movement mechanism (31*d*) configured to move the first illumination optical systems 31L and 31R mutually independently or integrally, and therefore the movement mechanism moves the first illumination optical systems 31L and 31R mutually independently or integrally in a direction intersecting the optical axis of the objective lens 20. Such a configuration makes it possible to conduct adjustment of the appearance condition (appearance state) of the subject's eye. In some aspects, the movement mechanism operates under the control of a controller (the controller 200 described later).

In some aspects, the optical axis OS is movable relative to the optical axis of the objective lens 20. The direction of the relative movement is a direction that intersects the optical axis of the objective lens 20, and the relative movement is represented by a displacement vector in which at least one of the x component and the y component is not zero. For example, the surgical microscope 10 includes a movement mechanism (32*d*) configured to move the second illumination optical system 32, and therefore the movement mechanism moves the second illumination optical system 32 in a direction that intersects the optical axis of the objective lens 20. With such a configuration, it becomes possible to conduct adjustment of the appearance condition (appearance state) of unevenness and irregularities of sites and tissues of the subject's eye. In some aspects, the movement mechanism operates under the control of a controller (the controller 200 described later).

As described above, the present aspect is configured such that the illumination optical system 30 is arranged at the position directly above the objective lens 20 (the position in the transmission direction of the dichroic mirror DM1) and the observation optical system 40 is arranged at the position in the reflection direction of the dichroic mirror DM1. For example, the observation optical system 40 may be arranged in such a manner that the angle formed by the optical axis of the observation optical system 40 and the plane perpendicular to the optical axis of the objective lens 20 (the xy plane) belongs to the range between −20 degrees and +20 degrees.

According to the configuration of the present aspect, the observation optical system 40, which generally has a longer optical path length than the illumination optical system 30, is arranged substantially parallel to the xy plane. Hence, the observation optical system 40 of the present aspect does not interfere with the surgeon's field of view while conventional surgical microscopes, whose observation optical system is oriented along the vertical direction in front of the surgeon's eyes, do. Therefore, the surgeon is capable of easily seeing the screen of the display device 3 arranged in front of the surgeon. In other words, the visibility of displayed information (images and videos of the subject's eye, and other various kinds of reference information) during surgery etc. is improved. In addition, since the housing is not placed in front of the surgeon's eyes, it does not give a sense of oppression to the surgeon, thereby reducing the burden on the surgeon.

The observation optical system 40 is an optical system for observation of an image formed based on return light of the illumination light incident from the subject's eye through the objective lens 20. In the present aspect, the observation optical system 40 guides the image to an image sensor of the imaging camera 60.

As described above, the observation optical system 40 includes the observation optical system for left eye 40L and the observation optical system for right eye 40R. The configuration of the observation optical system for left eye 40L and the configuration of the observation optical system for right eye 40R are the same as or similar to one another. In some aspects, the observation optical system for left eye 40L and the observation optical system for right eye 40R may be configured in such a manner that their optical arrangements can be changed independently of each other. The observation optical system for left eye 40L and the observation optical system for right eye 40R function as a pair of photography systems.

The zoom expander 50 is also referred to as a beam expander, a variable beam expander, or the like. The zoom expander 50 includes the zoom expander for left eye 50L and the zoom expander for right eye 50R. The configuration of the zoom expander for left eye 50L and the configuration of the zoom expander for right eye 50R are the same as or similar to each other. In some aspects, the zoom expander for left eye 50L and the zoom expander for right eye 50R may be configured in such a manner that their optical arrangements can be changed independently of each other.

The zoom expander for left eye 50L includes the plurality of zoom lenses 51L, 52L, and 53L. At least one of the zoom lenses 51L, 52L, and 53L is movable in the direction along the optical axis with a variable magnification mechanism (not shown in the drawings).

Similarly, the zoom expander for right eye 50R includes the plurality of zoom lenses 51R, 52R, and 53R, and at least one of the zoom lenses 51R, 52R, and 53R is movable in the direction along the optical axis with a variable magnification mechanism (not shown in the drawings).

The variable magnification mechanism(s) may be configured to move a zoom lens of the zoom expander for left eye 50L and a zoom lens of the zoom expander for right eye 50R mutually independently or integrally in the directions along the optical axes. As a result of this, the magnification ratio for photographing the subject's eye is changed. In some aspects, the variable magnification mechanism(s) operates under the control of a controller (the controller 200 described later).

The diaphragm 55 is an optical element configured for adjusting the amount of light passing therethrough. In other words, the diaphragm 55 is an optical element for adjusting the amount of light directed to the imaging camera 60. The diaphragm 55 includes the diaphragm for left eye 55L and the diaphragm for right eye 55R. The diaphragm for left eye 55L and the diaphragm for right eye 55R are controlled independently of each other by a controller (the controller 200 described later).

The diaphragm for left eye 55L of a typical configuration has an opening (aperture) through which light passes and a blocking part that blocks light. The outer edge of the aperture corresponds to the inner edge of the blocking part. In other words, the aperture is defined by the blocking part. The diaphragm for left eye 55L is a variable diaphragm, and the type of this variable diaphragm may be freely selected or determined. For example, the diaphragm for left eye 55L may be any one of an iris diaphragm, a rotating diaphragm, a water gate (sluice) diaphragm, and a Waterhouse stop. The diaphragm for right eye 55R may have the same or similar configuration as or to the diaphragm for left eye 55L.

When a condition of the diaphragm for left eye 55L (i.e., the size (measurement, dimension, diameter) of the aperture) is changed, the amount of light directed to the imaging camera for left eye 60L changes. Specifically, when the size of the aperture of the diaphragm for left eye 55L is reduced (that is, when the aperture of the diaphragm for left eye 55L is narrowed down), the depth of focus (depth of field) of the observation optical system for left eye 40L increases and the area in focus becomes wider. However, this reduces the amount of light directed to the imaging camera for left eye 60L and thus, an image acquired by the imaging camera for left eye 60L becomes darker (i.e., the brightness of this image decreases). Conversely, when the size of the aperture of the diaphragm for left eye 55L is increased (that is, when the aperture of the diaphragm for left eye 55L is opened), the amount of light directed to the imaging camera for left eye 60L increases and thus, an image acquired by the imaging camera for left eye 60L becomes brighter (i.e., the brightness of this image increases). However, this decreases the depth of focus (depth of field) of the observation optical system for left eye 40L and thus, the area in focus becomes narrower.

When a condition of the diaphragm for right eye 55R (i.e., the size (diameter) of the aperture) is changed, the amount of light directed to the imaging camera for right eye 60R changes. Specifically, when the size of the aperture of the diaphragm for right eye 55R is reduced, the depth of focus (depth of field) of the observation optical system for right eye 40R increases and the area in focus becomes wider. However, this reduces the amount of light directed to the imaging camera for right eye 60R and thus, an image acquired by the imaging camera for right eye 60R becomes darker (i.e., the brightness of this image decreases). Conversely, when the size of the aperture of the diaphragm for right eye 55R is increased, the amount of light directed to the imaging camera for right eye 60R increases and thus, an image acquired by the imaging camera for right eye 60R becomes brighter (i.e., the brightness of this image increases). However, this decreases the depth of focus (depth of field) of the observation optical system for right eye 40R and thus, the area in focus becomes narrower.

The imaging camera 60 is a device that photographs an image formed by the observation optical system 40 and generates digital image data. The imaging camera 60 is typically a digital camera (digital video camera). The imaging camera 60 includes the imaging camera for left eye 60L and the imaging camera for right eye 60R. The configuration of the imaging camera for left eye 60L and the configuration of the imaging camera for right eye 60R are the same as or similar to one another. In some aspects, the imaging camera for left eye 60L and the imaging camera for right eye 60R may be configured in such a manner that their optical arrangements can be changed independently of each other.

The imaging camera for left eye 60L includes the imaging lens 61L and the image sensor 62L. The imaging lens 61L forms an image based on the return light that has passed through the diaphragm for left eye 55L, on the imaging surface (light receiving surface) of the image sensor 62L. The image sensor 62L is an area sensor, and may typically be a charge-coupled device (CCD) image sensor or a complementary metal oxide semiconductor (CMOS) image sensor. The image sensor 62L operates under the control of a controller (the controller 200 described later).

The imaging camera for right eye 60R includes the imaging lens 61R and the image sensor 62R. The imaging lens 61R forms an image based on the return light that has passed through the diaphragm for right eye 55R, on the imaging surface (light receiving surface) of the image sensor 62R. The image sensor 62R is an area sensor, and may typically be a CCD image sensor or a CMOS image sensor. The image sensor 62R operates under the control of a controller (the controller 200 described later).

<Processing System>

Figure 3:
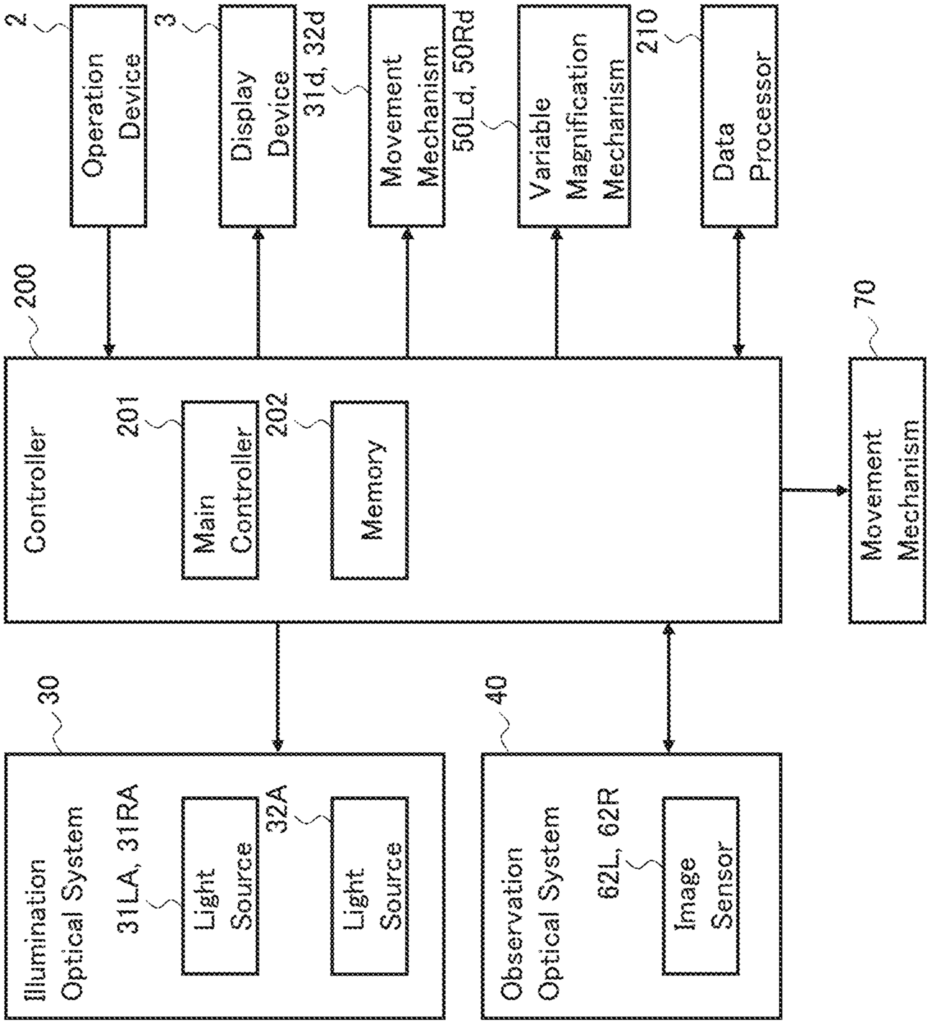
FIG. 3 is a diagram illustrating an example of a configuration of an ophthalmic observation apparatus according to an embodiment example.
Figure 4A:
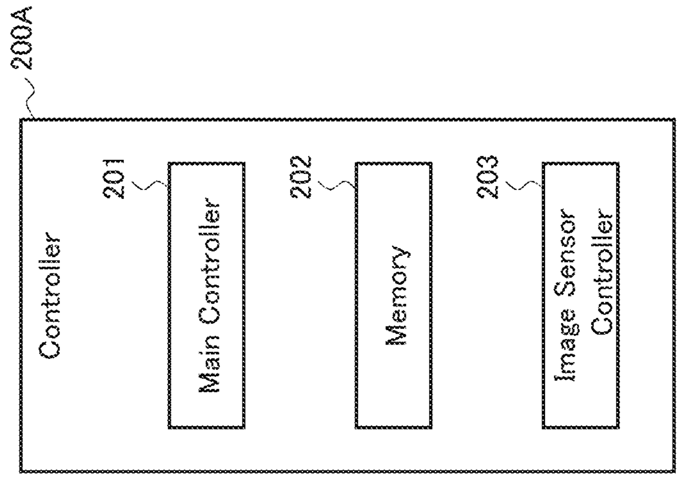
FIG. 4A is a diagram illustrating an example of a configuration of an ophthalmic observation apparatus according to an embodiment example.
Figure 4B:
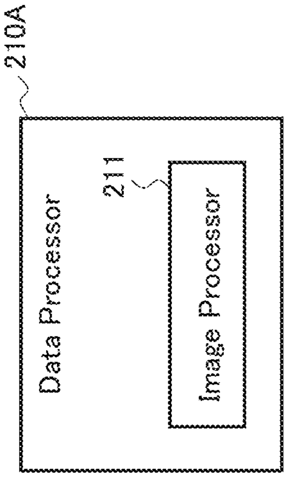
FIG. 4B is a diagram illustrating an example of a configuration of an ophthalmic observation apparatus according to an embodiment example.

The processing system of the ophthalmic observation apparatus 1 will be described. Some configuration examples of the processing system are shown in FIG. 3, FIG. 4A, and FIG. 4B. Any two or more of the various kinds of configuration examples described below may be combined at least in part. For example, the configuration example of FIG. 3 can be combined with the configuration example of FIG. 4A, the configuration example of FIG. 3 can be combined with the configuration example of FIG. 4B, and the configuration example of FIG. 3 can be combined with both the configuration example of FIG. 4A and the configuration example of FIG. 4B. Note that the configuration of the processing system is not limited to the examples described below.

The controller 200 executes a control of each part of the ophthalmic observation apparatus 1. The controller 200 includes the main controller 201 and the memory 202. The main controller 201 includes a processor and executes a control of each part of the ophthalmic observation apparatus 1. For example, the processor may load and run a program stored in the memory 202 or another storage device, thereby implementing a function according to the present aspect. In addition, the processor may use (e.g., referring, processing, calculating, etc.) data and/or information stored in the memory 202 or another storage device in order to implement a function according to the present aspect.

The main controller 201 may execute the following controls: a control of each of the light sources 31LA, 31RA, and 32A of the illumination optical system 30; a control of each of the diaphragms 55L and 55R of the observation optical system 40; a control of each of the image sensors 62L and 62R of the observation optical system 40; a control of each of the movement mechanisms 31*d* and 32*d*; a control of each of the variable magnification mechanisms 50Ld and 50Rd; a control of the operation device 2; a control of the display device 3; and a control of other component parts.

Controls of the light source 31LA include turning on and off the light source, adjusting the light amount, adjusting the illumination diaphragm (aperture), and so forth. Controls of the light source 31RA include turning on and off the light source, adjusting the light amount, adjusting the illumination diaphragm (aperture), and so forth. The main controller 201 may perform mutually exclusive control of the light sources 31LA and 31RA. Controls of the light source 32A include turning on and off the light source, adjusting the light amount, adjusting the illumination diaphragm (aperture), and so forth.

In the case where the illumination optical system 30 includes a light source whose color temperature can be varied, the main controller 201 may change the color temperature of emitted illumination light by controlling such a light source.

Controls of the image sensor 62L include exposure adjustment, gain adjustment, photographing rate adjustment, and so forth. Controls of the image sensor 62R include exposure adjustment, gain adjustment, photographing rate adjustment, and so forth. Further, the main controller 201 may control the image sensors 62L and 62R in such a manner that the photographing timings of the image sensors 62L and 62R match each other, or control the image sensors 62L and 62R in such a manner that the difference between the photographing timings of the image sensors 62L and 62R lies within a predetermined time. In addition, the main controller 201 may perform a control of loading digital data obtained by the image sensors 62L and 62R.

The movement mechanism 31*d* moves the light sources 31LA and 31RA mutually independently or integrally in a direction that intersects the optical axis of the objective lens 20. By controlling the movement mechanism 31*d*, the main controller 201 moves the optical axes OL and OR mutually independently or integrally with respect to the optical axis of the objective lens 20.

The movement mechanism 32*d* moves the light source 32A in a direction that intersects the optical axis of the objective lens 20. By controlling the movement mechanism 32*d*, the main controller 201 moves the optical axis OS with respect to the optical axis of the objective lens 20.

The movement mechanism 70 moves the surgical microscope 10. For example, the movement mechanism 70 is configured to integrally move at least part of the illumination optical system 30 and the observation optical system 40. This configuration makes it possible to change the relative positions of the at least part of the illumination optical system 30 and the observation optical system 40 with respect to the subject's eye while maintaining the relative positional relationship between at least part of the illumination optical system 30 and the observation optical system 40. In some aspects, the movement mechanism 70 is configured to integrally move the first illumination optical systems 31L and 31R and the observation optical system 40. With this, the relative positions of the first illumination optical systems 31L and 31R with respect to the subject's eye and the relative position of the observation optical system 40 with respect to the subject's eye can be changed while maintaining the state (condition) of coaxial illumination. In some aspects, the movement mechanism 70 is configured to integrally move the second illumination optical system 32 and the observation optical system 40. With this, the relative positions of the second illumination optical system 32 and the observation optical system 40 with respect to the subject's eye can be changed while maintaining the illumination angle for oblique illumination. In some aspects, the movement mechanism 70 is configured to integrally move the first illumination optical systems 31L and 31R, the second illumination optical system 32, and the observation optical system 40. This makes it possible to change the relative positions of the illumination optical system 30 and the observation optical system 40 with respect to the subject's eye while maintaining both the state (condition) of coaxial illumination and the illumination angle for oblique illumination. The movement mechanism 70 operates under a control of the controller 200.

In some aspects, the main controller 201 may be configured to control at least two of the movement mechanisms 31*d*, 32*d*, and 70 in an interlocking manner.

The variable magnification mechanism 50Ld moves at least one of the plurality of zoom lenses 51L to 53L of the zoom expander for left eye 50L in the optical axis direction (direction along the optical axis). The main controller 201 changes the magnification ratio of the observation optical system for left eye 40L by controlling the variable magnification mechanism 50Ld.

Similarly, the variable magnification mechanism 50Rd moves at least one of the plurality of zoom lenses 51R to 53R of the zoom expander for right eye 50R in the optical axis direction (direction along the optical axis). The main controller 201 changes the magnification ratio of the observation optical system for right eye 40R by controlling the variable magnification mechanism 50Rd.

Controls for the operation device 2 include an operation permission control, an operation prohibition control, an operation signal transmission control and/or an operation signal reception control from the operation device 2, and other controls. The main controller 201 receives an operation signal generated by the operation device 2 and executes a control corresponding to the operation signal received.

Controls for the display device 3 include an information display control and other controls. As a display controller, the main controller 201 displays an image based on digital image data generated by the image sensors 62L and 62R on the display device 3. Typically, the main controller 201 may display a pair of moving images (a pair of videos, a pair of movies) in parallel based on a pair of moving image data (video signals) respectively generated in parallel by the image sensors 62L and 62R on the display device 3. Further, the main controller 201 may display a still image (frame) included in one of the pair of moving images on the display device 3. In addition, the main controller 201 may display an image (a moving image, a still image, etc.) obtained by processing the digital image data generated by the image sensors 62L and 62R on the display device 3. Furthermore, the main controller 201 may display, on the display device 3, any information generated by the ophthalmic observation apparatus 1, any information acquired from the outside by the ophthalmic observation apparatus 1, and other types of information.

The main controller 201 is configured to function as a display controller of the present embodiment. In the first example of functioning as the display controller, the main controller 201 may display a moving image for left eye by sequentially displaying, on the display device 3, digital image data (frames) that are sequentially generated as moving image data for left eye by the image sensor 62L, while displaying a moving image for right eye by sequentially displaying, on the display device 3, digital image data (frames) that are sequentially generated as moving image data for right eye by the image sensor 62R that is operated in synchronization with the image sensor 62L. Here, the display of the moving image for left eye and the display of the moving image for right eye are operated in synchronization with each other. In other words, the main controller 201 substantially simultaneously displays a left frame and a right frame that are substantially simultaneously obtained by the left and right image sensors 62L and 62R on the display device 3. This first example may be employed, for example, in the case where the configuration shown in FIG. 4A (details will be described below) is applied.

In the second example of the main controller 201 functioning as a display controller, the moving image data acquired by the observation optical system 40 is processed by the data processor 210 and then displayed on the display device 3 by the main controller 201. The data processor 210 may sequentially apply predetermined processing (image processing) to digital image data (frames) that are sequentially generated as moving image data for left eye by the image sensor 62L, while sequentially applying predetermined processing (image processing) to digital image data (frames) that are sequentially generated as moving image data for right eye by the image sensor 62R that is operated in synchronization with the image sensor 62L. Here, the processing of the moving image data for left eye and the processing of the moving image data for right eye may be executed in synchronization with each other. In other words, the data processor 210 may execute parallel processing (simultaneous processing) of left and right frames that are substantially simultaneously obtained by the left and right image sensors 62L and 62R. The left and right frames processed in parallel are sent to the main controller 201 as a pair of frames, that is, as frames associated with each other, for example. The main controller 201 receives such pairs of frames (frames for left eye and frames for right eye) sequentially input from the data processor 210, and may display a moving image for left eye by sequentially displaying on the display device 3 the frames for left eye that are sequentially input, and also at the same time, display a moving image for right eye by sequentially displaying on the display device 3 the frames for right eye that are sequentially input. Here, the display of the moving image for left eye and the display of the moving image for right eye are executed in synchronization with each other. With this, the main controller 201 can substantially simultaneously display frames obtained substantially simultaneously by the left and right image sensors 62L and 62R on the display device 3. This second example may be employed, for example, in the case where the configuration shown in FIG. 4B (details will be described below) is applied.

The main controller 201 that functions as the display controller may be configured to display a moving image for left eye and a moving image for right eye on the display device 3 in such a manner as to enable stereoscopic vision. Here, the moving image for left eye and the moving image for right eye may be those obtained by means of at least one of the processing of the first example and the processing of the second example described above. For example, the main controller 201 may create a pair of left and right parallax images from the frame for left eye and the frame for right eye that have been obtained substantially simultaneously, and then display the pair of parallax images on the display device 3. With this, the user (e.g., surgeon) can recognize the pair of parallax images as a stereoscopic image by using a known stereoscopic method or technique. The stereoscopic method applicable to the present aspect may be freely selected, and for example, may be any of the following methods: a stereoscopic method for naked eyes; a stereoscopic method using an auxiliary device (polarized glasses, etc.); a stereoscopic method by applying image processing (image synthesis, image composition, rendering, etc.) to a frame for left eye and a frame for right eye; a stereoscopic method by displaying a pair of parallax images simultaneously; a stereoscopic method by alternately displaying a pair of parallax images; and a stereoscopic method of a combination of two or more of the above methods.

The data processor 210 executes various kinds of data processes. Some examples of processing that may be executed by the data processor 210 will be described below. The data processor 210 (each element thereof) includes a processor that operates on the basis of predetermined software (program), and is implemented by the cooperation of hardware and software.

The ophthalmic observation apparatus 1 of the present embodiment is configured to acquire moving image data for the left eye of the subject and moving image data for the right eye of the subject using the surgical microscope 10 that includes the observation optical system for left eye 40L and the observation optical system for right eye 40R, and then perform predetermined processing (first processing) in such a manner that a predetermined parameter of the moving image data for the left eye and the moving image data for the right eye satisfies a predetermined condition (first condition), and then display a moving image for the left eye and a moving image for the right eye based on the moving image data for the left eye and the moving image data for the right eye produced by the first processing.

Here, the predetermined parameter of moving image data may be freely selected or determined, and may be, for example, the brightness (luminance) of frames.

In addition, the first processing may be freely selected or determined, and may include, for example, a control of the surgical microscope 10 and/or image processing applied to at least one of the moving image data for the left eye and the moving image data for the right eye. In other words, the first processing may include at least one of this control and this image processing. The control of the surgical microscope 10 is performed by the controller 200 and may be performed, for example, by the image sensor controller 203 shown in FIG. 4A. The image processing for at least one of the moving image data for the left eye and the moving image data for the right eye is performed by the data processor 210, and may be performed by the image processor 211 shown in FIG. 4B, for example.

The first condition may be freely selected or determined, and may be, for example, that a predetermined parameter condition for the moving image data for the left eye and a predetermined parameter condition for the moving image data for the right eye become the same (equal, equivalent). The first condition of this example (equalization of parameter condition) may be, for example, either that both parameter values are equal, or that a difference between both parameter values is less than a predetermined threshold value.

In some embodiments, the ophthalmic observation apparatus 1 is configured to acquire moving image data for the left eye of the subject and moving image data for the right eye of the subject using the surgical microscope 10 that includes the observation optical system for left eye 40L and the observation optical system for right eye 40R, and then perform the first processing in such a manner that corresponding left and right frames in the moving image data for the left eye and the moving image data for the right eye have the same (equivalent) brightness, and then display a moving image for the left eye and a moving image for the right eye based on the moving image data for the left eye and the moving image data for the right eye produced by the first processing, that is, based on the moving image data for the left eye and the moving image data for the right eye in which brightness values between corresponding frames are equalized.

Several configuration examples for implementing the ophthalmic observation apparatus 1 having the above functions are described below. FIG. 4A shows the first configuration example, and FIG. 4B shows the second configuration example. It should be noted that the configuration for implementing brightness equalization between corresponding frames is not limited to these examples.

The purpose of the first processing is not limited to the equalization of the brightness between corresponding frames, and may be freely selected or determined. For example, the parameter of moving image data considered in the first processing is not limited to the brightness parameter, and may be a parameter of any type. The number of parameters considered in the first processing may also be freely selected or determined. Examples of parameters of moving image data that can be considered in the first processing include parameters of the following types: a color tone parameter, a contrast parameter, a gamma parameter, a color temperature parameter, a white balance parameter, an RGB balance parameter, a gray balance parameter, an edge enhancement parameter, a shadow enhancement parameter, a sharpening parameter, and a high dynamic range parameter.

The purpose of the first processing is not limited to the equalization of left and right parameter conditions. The purpose of the first processing may be freely selected or determined. The purpose of the first processing may be any of the following examples: making left and right parameters have different values whose difference is equal to or greater than a predetermined threshold value, making values of left and right parameters belong to a predetermined range, and making the value of another parameter obtained from left and right parameters satisfies a predetermined condition.

Both the configuration example shown in FIG. 4A and the configuration example shown in FIG. 4B function to compensate for a difference in the moving image parameters caused by a difference in a photography condition between the observation optical system for left eye 40L and the observation optical system for right eye 40R. More specifically, both the configuration example shown in FIG. 4A and the configuration example shown in FIG. 4B function to cancel out a difference (eliminate a difference, or make a difference smaller than a threshold value) between the brightness of the moving image data for left eye and the brightness of the moving image data for right eye caused by a difference between a condition of the diaphragm for left eye 55L of the observation optical system for left eye 40L and a condition of the diaphragm for right eye 55R of the observation optical system for right eye 40R.

The first configuration example shown in FIG. 4A relates to the configuration of the controller 200. The controller 200A in the present example is an example of the controller 200 and includes the image sensor controller 203. The image sensor controller 203 functions as a processor that executes the first processing, and is configured to control at least one of the image sensor 62L of the observation optical system for left eye 40L and the image sensor 62R of the observation optical system for right eye 40R in order to compensate for the difference between the brightness in the moving image data for left eye and the brightness in the moving image data for right eye.

In the present example, the image sensor controller 203 is configured to control at least one of a gain of the image sensor 62L of the observation optical system for left eye 40L and a gain of the image sensor 62R of the observation optical system for right eye 40R.

In this control, the gain adjustment amount may be, for example, determined by the image sensor controller 203 based on the amount of the difference (e.g., a value obtained by subtraction, ratio, etc.) between a condition of the diaphragm for left eye 55L (the size of the aperture thereof) and a condition of the diaphragm for right eye 55R (the size of the aperture thereof).

A description will be given of the first example. The image sensor controller 203 of the present example stores in advance information on a unit gain adjustment amount that corresponds to a unit difference amount between the conditions of the left and right diaphragms. The image sensor controller 203 of the present example may be configured to receive the condition of the diaphragm for left eye 55L and the condition of the diaphragm for right eye 55R from the main controller 201, then calculate the difference amount between these conditions, then divide the calculated difference amount by the unit difference amount, and then determine a gain adjustment amount based on the quotient obtained by this division and the unit gain adjustment amount.

A description will be given of the second example. The image sensor controller 203 of the present example stores in advance information on a correspondence (relationship, association) between difference amounts between the conditions of the left and right diaphragms and gain adjustment amounts. This information is referred to as correspondence information. The image sensor controller 203 of the present example may be configured to receive the condition of the diaphragm for left eye 55L and the condition of the diaphragm for right eye 55R from the main controller 201, then calculate the difference amount between these conditions, and then determine a gain adjustment amount corresponding to the calculated difference amount by referring to the correspondence information. The correspondence information may be, for example, a table or a graph.

When the size of the aperture of the diaphragm for left eye 55L is smaller than the size of the aperture of the diaphragm for right eye 55R, the image sensor controller 203 may perform, for example, a control to increase the gain of the image sensor 62L of the observation optical system for left eye 40L, a control to decrease the gain of the image sensor 62R of the observation optical system for right eye 40R, or both of these two controls. As a result of this, the difference in brightness between the left moving image data and the right moving image data caused by the difference in conditions between the left and right diaphragms (apertures) can be reduced. For example, the brightness of the left moving image data and the brightness of the right moving image data can be made equal.

Conversely, when the size of the aperture of the diaphragm for left eye 55L is larger than the size of the aperture of the diaphragm for right eye 55R, the image sensor controller 203 may perform, for example, a control to increase the gain of the image sensor 62R of the observation optical system for right eye 40R, a control to decrease the gain of the image sensor 62L of the observation optical system for left eye 40L, or both of these controls. As a result of this, the difference in brightness between the left moving image data and the right moving image data caused by the difference in conditions between the left and right diaphragms (apertures) can be reduced. For example, the brightness of the left moving image data and the brightness of the right moving image data can be equalized.

With this function of the image sensor controller 203, the ophthalmic observation apparatus 1 can not only present a moving image with high resolution and a moving image with a wide depth of field in parallel, but also display both the moving images with equivalent brightness. This allows the user to conduct observation of the first moving image having a wide area (wide range) in focus with the left eye (or the right eye) while conducting observation of a moving image having equivalent brightness to the first moving image and also having high resolution with the right eye (or the left eye) during ophthalmic surgery.

Some of the above examples are configured to perform gain adjustment on the basis of the difference in the conditions of the left and right diaphragms; however, the processing executable by the ophthalmic observation apparatus 1 is not limited to such an aspect of gain adjustment. In some examples, the controller 200 may be configured to refer to information on a correspondence (relationship, association) between difference amounts between the conditions of the left and right diaphragms and gain adjustment amounts (this information is referred to as correspondence information), to perform the following controls in an interlocking manner: a control of at least one of the diaphragm for left eye 55L and the diaphragm for right eye 55R by the main controller 201; and a control of at least one of the image sensor 62L of the observation optical system for left eye 40L and the image sensor 62R of the observation optical system for right eye 40R by the image sensor controller 203.

The second configuration example shown in FIG. 4B relates to the configuration of the data processor 210. The data processor 210A of the present example is an example of the data processor 210 and includes the image processor 211. The image processor 211 functions as a processor that performs the first processing and is configured to execute adjustment of the brightness of at least one of the moving image data for left eye and the moving image data for right eye in order to compensate for the difference between the brightness of the moving image data for left eye and the brightness of the moving image data for right eye.

Here, the adjustment amount of the brightness of moving image data is, for example, determined by the image processor 211 based on the amount of the difference (e.g., a value obtained by subtraction, ratio, etc.) between a condition of the diaphragm for left eye 55L (the size of the aperture thereof) and a condition of the diaphragm for right eye 55R (the size of the aperture thereof). In addition, the method or technique employed for calculating the brightness of moving image data (the frames thereof) and the method or technique employed for changing the brightness of moving image data (the frames thereof) may be selected from known methods or techniques.

A description will be given of the first example. The image processor 211 of the present example stores in advance information on a unit brightness adjustment amount that corresponds to a unit difference amount of the conditions of the left and right diaphragms. The image processor 211 of the present example may be configured to receive the condition of the diaphragm for left eye 55L and the condition of the diaphragm for right eye 55R from the main controller 201, then calculate the difference amount between these conditions, then divide the calculated difference amount by the unit difference amount, and then determine a brightness adjustment amount (a parameter used in image processing for brightness adjustment) based on the quotient obtained from the division and the unit brightness adjustment amount.

A description will be given of the second example. The image processor 211 of the present example stores in advance information on a correspondence (relationship, association) between difference amounts between the conditions of the left and right diaphragms and brightness adjustment amounts. This information is referred to as correspondence information. The image processor 211 of the present example may be configured to receive the condition of the diaphragm for left eye 55L and the condition of the diaphragm for right eye 55R from the main controller 201, then calculate the difference amount between these conditions, and then determine a brightness adjustment amount corresponding to the calculated difference amount by referring to the correspondence information. The correspondence information may be, for example, a table or a graph.

When the size of the aperture of the diaphragm for left eye 55L is smaller than the size of the aperture of the diaphragm for right eye 55R, the image processor 211 may perform, for example, image processing to increase the brightness of the moving image data for the left eye, image processing to decrease the brightness of the moving image data for the right eye, or both of these two kinds of image processing. As a result of this, the difference in brightness between the left moving image data and the right moving image data caused by the difference in conditions between the left and right diaphragms (apertures) can be reduced. For example, the brightness of the left moving image data and the brightness of the right moving image data can be equalized.

Conversely, when the size of the aperture of the diaphragm for left eye 55L is larger than the size of the aperture of the diaphragm for right eye 55R, the image processor 211 may perform, for example, image processing to increase the brightness of the moving image data for the right eye, image processing to decrease the brightness of the moving image data for the left eye, or both of these two kinds of image processing. As a result of this, the difference in brightness between the left moving image data and the right moving image data caused by the difference in conditions between the left and right diaphragms (apertures) can be reduced. For example, the brightness of the left moving image data and the brightness of the right moving image data can be made equal.

With this function of the image processor 211, the ophthalmic observation apparatus 1 can not only present a moving image with high resolution and a moving image with a wide depth of field in parallel, but also display both the moving images with equivalent brightness. This allows the user to conduct observation of the first moving image having a wide area (wide range) in focus with the left eye (or the right eye) while conducting observation of a moving image having equivalent brightness as the first moving image and also having high resolution with the right eye (or the left eye) during ophthalmic surgery.

Some of the above examples are configured to perform image processing for brightness adjustment on the basis of the difference in the conditions of the left and right diaphragms; however, the processing executable by the ophthalmic observation apparatus 1 is not limited to such an aspect of image processing for brightness adjustment. In some examples, the controller 200 and the data processor 210 may be configured to refer to information on a correspondence (relationship, association) between difference amounts between the conditions of the left and right diaphragms and brightness adjustment amounts (a parameter used in image processing) (this information is referred to as correspondence information), to perform the following control and the following image processing in an interlocking manner: a control of at least one of the diaphragm for left eye 55L and the diaphragm for right eye 55R by the main controller 201; and image processing of at least one of the moving image data for the left eye and the moving image data for the right eye by the image processor 211.

The ophthalmic observation apparatus 1 of some aspects may be configured to be capable of performing the second processing in addition to the first processing described above. A purpose of the second processing is to make the brightness of the left moving image data and the brightness of the right moving image data satisfy the second condition, and the second processing includes at least one of a control of the surgical microscope 10 and image processing of at least one of the left moving image data and the right moving image data. A processing item (processing content) executed in the second processing may be the same as or different from the processing item executed in the first processing. For example, in the case where the processing item of the first processing is gain adjustment, the processing item of the second processing may be any of gain adjustment, brightness adjustment (image processing), other processing items, and combinations of any two or more of these items. Further, in the case where the processing item of the first processing is brightness adjustment (image processing), the processing item of the second processing may be any of brightness adjustment, gain adjustment, other processing items, and combinations of any two or more of these items. In addition, in the case where the processing item of the first processing is neither gain adjustment nor brightness adjustment (image processing), the processing item of the second processing may be any of gain adjustment, brightness adjustment, other processing items, and combinations of any two or more of these items.

A specific example of the second processing will be described. The purpose of the second processing of the present example is to make the brightness of the left moving image data and the brightness of the right moving image data equal to or greater than a predetermined threshold value. The image sensor controller 203 of the present example may be configured to perform at least one of gain adjustment (increase in gain) of the image sensor 62L of the observation optical system for left eye 40L and gain adjustment (increase in gain) of the image sensor 62R of the observation optical system for right eye 40R in such a manner that both the brightness of the moving image data for the left eye and the brightness of the moving image data for the right eye become equal to or greater than a threshold value. In addition to or in place of this, the image processor 211 of the present example may be configured to perform at least one of image processing on the moving image data for the left eye and image processing on the moving image data for the right eye in such a manner that both the brightness of the moving image data for the left eye and the brightness of the moving image data for the right eye become equal to or greater than a threshold value.

By carrying out such second processing, it becomes possible to present a moving image with sufficient brightness, that is, a moving image with sufficient resolution, to both eyes of the user.

<Operation and Usage Mode>

Figure 5:
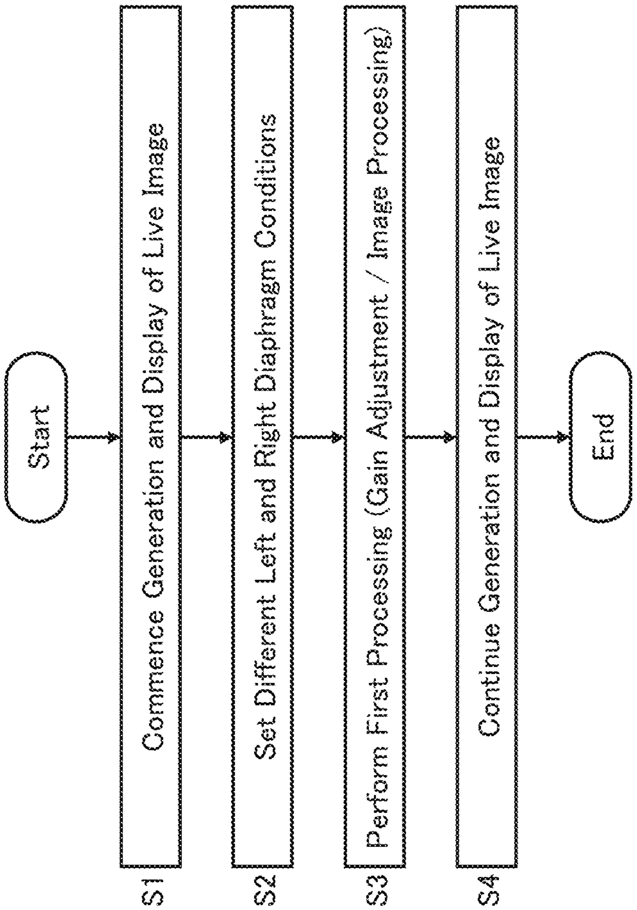
FIG. 5 is a flowchart illustrating an example of processing performed by an ophthalmic observation apparatus according to an embodiment example.

The operation and the usage mode of the ophthalmic observation apparatus 1 will be described below. An example of the operation and the usage mode of the ophthalmic observation apparatus 1 is shown in FIG. 5.

The present example gives a description of a case of performing compensation for a difference in a predetermined parameter (brightness) between left moving image data and right moving image data that is caused by a difference in a predetermined photography condition (diaphragm condition (depth of focus, depth of field)) between a left photography system and a right photography system of a digital binocular surgical microscope. It should be noted that substantially the same operation and usage mode as in the present example can also be implemented in the following cases, except for differences related to a specific characteristic of an ophthalmic observation apparatus to which the operation and usage mode are applied and a specific characteristic of matters and items to be taken into consideration: a case of applying the present example to an ophthalmic observation apparatus other than a surgical microscope; a case of taking a photography condition other than a diaphragm condition into account; a case of taking a condition other than a photography condition into account; and a case of taking a moving image parameter other than brightness into account.

(S1: Commence Generation and Display of Live Image)

First, the user performs a predetermined operation using the operation device 2 to make the ophthalmic observation apparatus 1 start generating and displaying a live image of the subject's eye (the anterior eye segment thereof). More specifically, the surgical microscope 10 illuminates the subject's eye by means of the illumination optical system 30 while generating moving image data for left eye and moving image data for right eye by means, respectively, of the observation optical system for left eye 40L and the observation optical system for right eye 40R. The main controller 201 displays a moving image for left eye on the basis of the moving image data for left eye and a moving image for right eye on the basis of the moving image data for right eye on the display device 3 in real time. The user can conduct surgery while observing the left and right live images.

(S2: Set Different Left and Right Diaphragm Conditions)

Next, the user (e.g., surgeon, operator, assistant, etc.) performs an operation using the operation device 2 in such a manner that the condition (the size of the aperture) of the diaphragm for left eye 55L and the condition (the size of the aperture) of the diaphragm for right eye 55R become different from each other. As a result of this operation, the surgical microscope 10 generates moving image data for the left eye and moving image data for the right eye that have mutually different depths of field and mutually different brightness, and a moving image for the left eye and a moving image for the right eye that have mutually different depths of field and mutually different brightness are displayed on the display device 3.

(S3: Perform First Processing)

In response to the operation of the step S2 being performed, the processor of the ophthalmic observation apparatus 1 performs the first processing to compensate for the brightness difference between the moving image for the left eye and the moving image for the right eye.

In the case where the image sensor controller 203 functions as the processor, the main controller 201 sends an instruction to the image sensor controller 203 in response to the operation of the step S2 being performed. Upon receiving the instruction, the image sensor controller 203 performs at least one of a control of a gain of the image sensor 62L of the observation optical system for left eye 40L and a control of a gain of the image sensor 62R of the observation optical system for right eye 40R, in order to compensate for the brightness difference between the moving image for the left eye and the moving image for the right eye. The gain control (gain adjustment) of the present step is performed in the manner described above. By the execution of the gain control, the brightness of the moving image data for the left eye output from the image sensor 62L and the brightness of the moving image data for the right eye output from the image sensor 62R become equivalent to one another. As a result of this, the user can have the moving image for the left eye and the moving image for the right eye not only with equivalent brightness but also with mutually different areas in focus.

In the case where the image processor 211 functions as the processor, the main controller 201 sends an instruction to the image processor 211 in response to the operation of the step S2 being performed. Upon receiving the instruction, the image processor 211 starts at least one of the following image processing (brightness adjustments) in order to compensate for the difference in brightness between the moving image for the left eye and the moving image for the right eye: image processing (brightness adjustment) performed on the moving image data for the left eye obtained by the image sensor 62L of the observation optical system for left eye 40L; and image processing (brightness adjustment) performed on the moving image data for the right eye obtained by the image sensor 62R of the observation optical system for right eye 40R. With this, the image processor 211 performs at least one of image processing for each of the frames for the left eye sequentially output from the image sensor 62L and image processing for each of the frames for the right eye sequentially output from the image sensor 62R. Such image processing is performed in the manner described above. When the image processing starts to be applied, the brightness of the moving image data for the left eye and the brightness of the moving image data for the right eye to be provided to the display device 3 become equivalent. As a result of this, the user can have the moving image for the left eye and the moving image for the right eye not only with equivalent brightness but also with mutually different areas in focus.

(S4: Continue Generation and Display of Live Image)

The ophthalmic observation apparatus 1 continues to generate the moving image data for the left eye and the moving image data for the right eye by the surgical microscope 10, and also continues to display the moving image for the left eye and the moving image for the right eye produced in the step S3, in other words, display the moving image for the left eye and the moving image for the right eye that have equivalent brightness and mutually different areas in focus (End).

The user can perform fine tuning (fine adjustment) of brightness, fine tuning of diaphragm (aperture) conditions, and other fine tuning, using the operation device 2. The surgeon (operator) can carry out surgery while observing the moving image for the left eye and the moving image for the right eye that have been adjusted in a desired manner (desired aspect, desired appearance, desired mode).

According to the operation and the usage mode of the present example, it is possible to perform gain adjustment of one of or both the left and right image sensors, and/or perform brightness adjustment of one of or both the left moving image data and the right moving image data, when the left diaphragm condition and right diaphragm condition of the digital binocular surgical microscope are made different from one another. Such linked (interlocking) operations (e.g., a linkage between diaphragm adjustment and gain adjustment, a linkage between diaphragm adjustment and brightness adjustment, and a linkage between diaphragm adjustment, gain adjustment, and brightness adjustment) can be used, for example, in the case where the aperture of one of the left and right photography systems is contracted, to increase the gain of the image sensor of the photography system whose aperture has been contracted and/or increase the brightness of the moving image data obtained by this photography system. With this, decrease in brightness of the moving image data obtained by the photography system whose aperture has been contracted can be compensated for, thereby making the brightness of the left moving image and the brightness of the right moving image balanced. This makes it possible to present in parallel both a moving image with resolution prioritized and a moving image with area in focus prioritized, while adjusting the brightness of these images equivalent. According to the present example, it becomes possible to use a digital ophthalmic observation apparatus to conduct the observation method or technique with different conditions for the left and right optical systems, which has been performed using an existing or conventional eyepiece-type (non-digital) binocular ophthalmic observation apparatus.

<Modification>

Several modification examples of the above embodiment will be described.

The embodiment described above is configured to automatically perform the gain adjustment corresponding to the difference between the left and right diaphragm conditions; however, this gain control may be performed manually. For example, the main controller 201 may be configured to display information to prompt the user to perform gain adjustment, information showing a gain adjustment amount, and/or information of other kinds on the display device 3, in response to occurrence of the fact that the left and right diaphragm conditions are set differently from one another.

The embodiment described above is configured to compensate for a difference in brightness between left and right moving images caused by a difference in conditions of left and right diaphragms. However, it should be noted that the cause of the brightness difference between the left and right moving images is not limited to the difference in the conditions of the left and right diaphragms. For example, when conducting the coaxial illumination described above, it is necessary to precisely position the optical system with respect to the subject's eye, and it is known that even a slight change in the position of the optical system can cause a change in the brightness of an obtained image (red reflex image, transillumination image). Accordingly, when coaxial illumination is performed with a digital binocular ophthalmic observation apparatus, there may be cases in which the brightness of a moving image for left eye and the brightness of a moving image for right eye differ from each other. If this is the case, as in the embodiment described above, gain adjustment and/or image processing (brightness adjustment) can be performed to equalize the brightness of the moving image for left eye and the brightness of the moving image for right eye with one another. Furthermore, a transillumination image is a reddish image, and there may be cases in which the color of a moving image for left eye and the color of a moving image for right eye may differ from each other. If this is the case, as in the case of brightness equalization, processing (image processing, etc.) can be performed to equalize a parameter related to image colors (e.g., a color tone parameter, a color temperature parameter, a RGB balance parameter, etc.), thereby making the color of the moving image for left eye and the color of the moving image for right eye equivalent.

The embodiments described in the present disclosure are merely examples, and any modification, omission, addition, substitution, etc. can be made within the scope of the present disclosure and its equivalents.

What is claimed is:

1. An ophthalmic observation apparatus comprising:

a microscope including a pair of photography systems configured to simultaneously photograph each of a subject's eyes to acquire a pair of pieces of moving image data of the subject's eyes, each of the pair of photography systems including an image sensor and a diaphragm configured to adjust an amount of light directed to the image sensor, and the microscope being configured to acquire the pair of pieces of moving image data that have mutually different brightness by photographing the subject's eyes with mutually different diaphragm conditions by the pair of photography systems, wherein the different diaphragm conditions include different aperture sizes for each of the pair of photography systems;

a processor configured to perform first processing including at least one of a control of the microscope and image processing applied to at least one of the pair of pieces of moving image data, such that a predetermined parameter of the pair of pieces of moving image data satisfies a first condition; and a display controller configured to display a pair of moving images based on the pair of pieces of moving image data produced by the first processing on a display device, wherein the processor is configured to perform the first processing in such a manner as to compensate for a difference in the brightness of the pair of moving images caused by the different diaphragm conditions between the pair of photography systems, the diaphragm in each of the pair of photography systems is further configured to increase and decrease a depth of field, the microscope is further configured to acquire the pair of pieces of moving image data that have the mutually different brightness and mutually different depths of field, and the processor is configured to perform the first processing to further compensate for the difference in the brightness and the mutually different depths of field in the pair of moving images caused by the different diaphragm conditions between the pair of photography systems.

2. The ophthalmic observation apparatus according to claim 1, wherein the processor is configured to perform the first processing in such a manner as to compensate for a difference in the parameter of the pair of moving images caused by a difference in a predetermined photography condition between the pair of photography systems.

3. The ophthalmic observation apparatus according to claim 2, wherein each of the pair of photography systems includes an image sensor, and a diaphragm configured for adjusting an amount of light directed to the image sensor, and the photography condition includes a condition of the diaphragm.

4. The ophthalmic observation apparatus according to claim 3, wherein the processor is configured to perform the first processing in such a manner as to compensate for a difference in brightness between the pair of moving images.

5. The ophthalmic observation apparatus according to claim 4, wherein the processor is configured to control a gain of the image sensor of at least one of the pair of photography systems in order to compensate for the difference in the brightness.

6. The ophthalmic observation apparatus according to claim 4, wherein the processor is configured to adjust brightness of at least one of the pair of pieces of moving image data in order to compensate for the difference in the brightness.

7. The ophthalmic observation apparatus according to claim 4, wherein the processor is configured to perform second processing including at least one of a control of the microscope and image processing applied to at least one of the pair of pieces of moving image data such that the brightness of the pair of moving images further satisfies a second condition.

8. The ophthalmic observation apparatus according to claim 7, wherein the processor is configured to perform the second processing such that the brightness of both the pair of moving images becomes equal to or greater than a predetermined threshold value.

9. The ophthalmic observation apparatus according to claim 1, wherein the processor is configured to perform the first processing in such a manner as to compensate for a difference in brightness between the pair of moving images.

* * * * *